US006856828B2

United States Patent
Cossette et al.

(10) Patent No.: US 6,856,828 B2
(45) Date of Patent: Feb. 15, 2005

(54) CAS BONE REFERENCE AND LESS INVASIVE INSTALLATION METHOD THEREOF

(75) Inventors: Sébastien Cossette, Montréal (CA); Herbert Jansen, Montréal (CA); Benoît Chouinard, Montréal (CA)

(73) Assignee: Orthosoft Inc., Montreal ( * ) Notice: Subject to any disclaimer, the term of this patent is extended or adjusted under 35 U.S.C. 154(b) by 124 days.

(21) Appl. No.: 10/263,708

(22) Filed: Oct. 4, 2002

(65) Prior Publication Data

US 2004/0068260 A1 Apr. 8, 2004

(51) Int. Cl.[7] .................................................. A61B 5/05
(52) U.S. Cl. ...................................................... 600/429
(58) Field of Search ................................ 600/429, 407, 600/424, 425–428; 378/21–4, 22–27; 606/130

(56) References Cited

U.S. PATENT DOCUMENTS

| | | | |
|---|---|---|---|
| 4,696,308 A | | 9/1987 | Meller et al. |
| 5,119,817 A | * | 6/1992 | Allen .......................... 600/426 |
| 5,211,164 A | * | 5/1993 | Allen .......................... 600/426 |
| 5,575,794 A | | 11/1996 | Santangelo et al. |
| 5,810,826 A | | 9/1998 | Akerfeldt et al. |
| 6,117,143 A | * | 9/2000 | Hynes et al. ................ 606/130 |
| 6,127,597 A | * | 10/2000 | Beyar et al. .................. 606/86 |
| 6,203,543 B1 | | 3/2001 | Glossop |
| 6,226,548 B1 | | 5/2001 | Foley et al. |
| 6,270,518 B1 | * | 8/2001 | Pedlick et al. .............. 606/232 |
| 6,529,765 B1 | * | 3/2003 | Franck et al. ............... 600/427 |
| 6,640,127 B1 | * | 10/2003 | Kosaka et al. ............. 600/426 |
| 6,665,554 B1 | * | 12/2003 | Charles et al. ............. 600/427 |
| 6,685,706 B2 | * | 2/2004 | Padget et al. ................. 606/72 |
| 2002/0107518 A1 | | 8/2002 | Brundobler et al. |

* cited by examiner

*Primary Examiner*—Daniel Robinson
(74) *Attorney, Agent, or Firm*—Ogilvy Renault (57) ABSTRACT

A surgical bone reference assembly is communicable with an image guided surgical system such that position and movement of a bone element are monitorable. A bone anchor member comprises a trackable member and teeth engageable with the bone element. The trackable member comprises a detectable element adapted to be located and tracked in three dimensional space by the image guided surgical system, thereby defining position and movement of the trackable member. A protective guide member is used with the bone anchor member such that the bone anchor member is insertable through soft tissue covering the bone element without causing significant damage thereto. The bone anchor member is engageable with the bone element, such that the teeth are forced into engagement with the bone element and the bone anchor member is fastenable to the bone element in a fixed relation thereto.

38 Claims, 6 Drawing Sheets

CAS BONE REFERENCE AND LESS INVASIVE INSTALLATION METHOD THEREOF

INCORPORATION BY REFERENCE

This application incorporate by reference patent application Ser. No.10/263,711 filed Oct. 4, 2002,titled "CAS Bone Reference With Articulated Support" commonly assigned to ORTHOsoft Inc. by Benoit Chouinard et al.

TECHNICAL FIELD

The present invention relates generally to a bone reference for use in conjunction with a computer assisted surgery (CAS) system. More particularly, the present invention relates to a trackable bone reference member engageable with a separately installed outer sleeve that limits invasiveness of the installation of the bone reference member.

BACKGROUND OF THE INVENTION

CAS systems capable of real time location and tracking of a plurality of discrete objects in a surgical field are now becoming increasingly well known. A variety of systems are employed, however all require the patient bone elements to be identified and registered to pre-operatively taken anatomical scans or intra-operatively taken images of the same bone elements. In order for the relevant bone elements to be located and tracked by the CAS system, trackable reference members must be fastened thereto. These bone reference members will vary depending on the type and specific requirement of the particular CAS system used.

For example, for an optical CAS system, the trackable bone reference members will comprise at least three optically detectable markers whose exact position can be determined by each of the at least two cameras of the optical CAS system. This therefore permits the position in space of each detectable marker to be determined by the CAS system, and therefore permits the position and orientation of the bone reference member, and consequently also the position and orientation of the bone element to which it is affixed, to be determinable by the CAS system.

However, installation of traditional bone reference members, which are identifiable by the CAS system and are fixed to each bone element, can often be significantly invasive to the patient. Relatively large incisions are sometimes required in order to expose a section of bone sufficiently large enough to accommodate the bone reference that is to be fastened thereto. Any unnecessary invasiveness can result in significant additional patient trauma and post-operative pain. As such, bone reference blocks that can be fastened to a bone element with a minimum amount of invasiveness have been more recently developed. For example, rather than having a reference block screwed directly to an exposed portion of a bone element, only positioning pins, inserted through relatively smaller incisions in the skin, are driven into the bone element. These pins are therefore anchored in the bone, and extend beyond the skin such that a reference block can be engaged to the exposed portions of the pins. This thereby permits reference members to be indirectly fixed to the bone elements via the pins which can be fastened to the bone element with a limited amount of invasiveness.

However, for certain particular applications, it can be necessary to use a bone reference member that is directly fastened to the bone element. Also, some surgical uses may not permit the obstructed space required for the relatively wider stance that the pined-type bone reference members occupy.

It is currently known in total hip replacement surgery to use a CAS femoral reference member that is elongated and comprises a toothed proximal end for direct engagement with the femur. The elongated body of the reference member is hollow, such that once the toothed end is engaged with the bone surface, a long cortical screw, such as a Trochar screw for example, can be inserted through the body of the reference member and fastened into the bone. A flange on the distal end of the screw serves to engage the distal end of the reference member and forces the teeth of the toothed proximal end thereof into the bone surface. The reference member is thereby axially and rotatably fixed relative to the bone element. A trackable member as described above is often integrally formed with the distal end of the reference member, thereby permitting the CAS system to determine the position and orientation of the bone reference member, and therefore track the movement of the bone element to which the reference member is fixed.

However, the installation of such a bone reference member also causes significant damage to soft tissue. Although it requires a smaller incision than the larger blocks that are fastened directly to the bone surface, the sharp teeth at the proximal end of the elongated body of such a bone reference member tend to cut and tear the surrounding soft tissue as the proximal end is inserted therethrough until it contacts the bone.

SUMMARY OF THE INVENTION

It is an object of the present invention to provide an improved bone reference member for use with a CAS system.

It is another object of the present invention to provide a CAS bone reference member that is directly fastened to a bone element.

It is another object of the present invention to provide a CAS bone reference member that generally reduces patient invasiveness.

It is another object of the present invention to provide a CAS bone reference member that only necessitates a small incision in the skin and which occupies a limited amount of space thereabove.

It is a further object of the present invention to provide a CAS bone reference member that reduces the amount of soft tissue damage caused during its installation on a bone element.

Therefore, in accordance with the present invention, there is provided a method for monitoring position and movement of a bone element using an image guided surgical system, comprising the steps of: providing a bone reference assembly comprising a toothed bone anchor member and a trackable member, the trackable member comprising a detectable element adapted to be located and tracked in three dimensional space by the image guided surgical system, thereby defining position and movement of the trackable member; inserting a protective guide member through soft tissue covering the bone element using a proximal end adapted for gradual separation of the soft tissue so as not to cause significant damage thereto, such that the proximal end is substantially adjacent the bone element, the protective guide member being sized to receive at least the toothed bone anchor member therein; using the protective guide member to guide the toothed bone anchor member into direct engagement with the bone element; engaging the toothed bone anchor member to the bone element such that the bone reference assembly is in a fixed position relative to the bone element; performing a registration of the bone element; and locating and tracking the bone element using the image guided surgical system.

There is also provided, in accordance with the present invention, a surgical bone reference assembly communicable with an image guided surgical system such that position and movement of a bone element are monitorable, the bone reference assembly comprising: a bone anchor member comprising a trackable member and teeth engageable with the bone element, the trackable member comprising a detectable element adapted to be located and tracked in three dimensional space by the image guided surgical system, thereby defining position and movement of the trackable member; and a protective guide member for use with the bone anchor member such that the bone anchor member is insertable through soft tissue covering the bone element without causing significant damage thereto; the bone anchor member being engageable with the bone element, such that the teeth are forced into engagement with the bone element and the bone anchor member is fastenable to the bone element in a fixed relation thereto.

BRIEF DESCRIPTION OF THE DRAWINGS

Further features and advantages of the present invention will become apparent from the following detailed description, taken in combination with the appended drawings, in which:

FIG. 5b is a top plan view of the alternate bone reference element of FIG. 5a.

FIG. 5c is a side elevation view of the alternate bone reference element of FIG. 5a.

DETAILED DESCRIPTION OF THE PREFERRED EMBODIMENT

Figure 1:
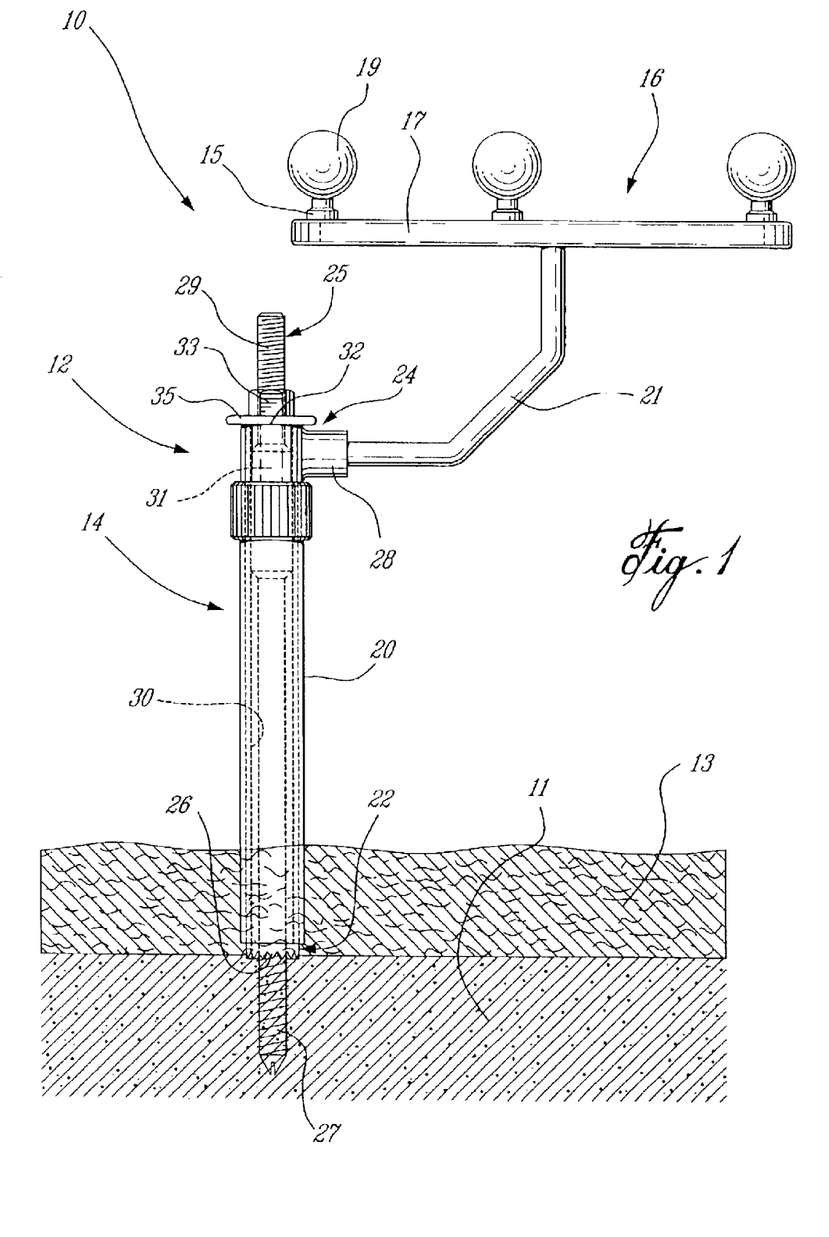
FIG. 1 is a front elevation view of the CAS reference assembly according to the present invention.

Referring to FIG. 1, the CAS body reference assembly 10 comprises generally a main bone reference element 12, a protective outer sleeve 14, a trackable member 16, and a cortical screw 25.

Figure 2:
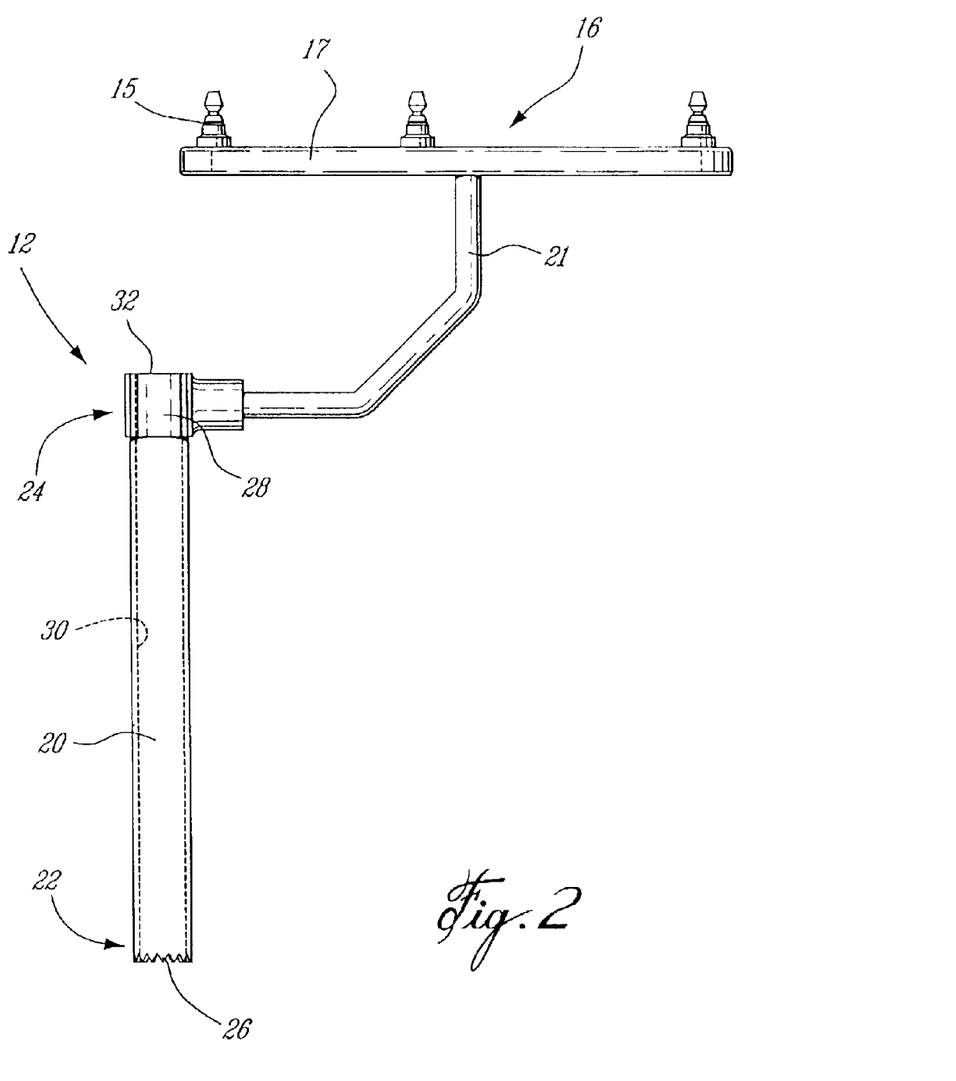
FIG. 2 is a front elevation view of the bone reference element of the CAS reference assembly of FIG. 1.

The bone reference element 12, seen alone in FIG. 2, comprises principally an elongated tubular body 20 having a proximal end 22 and a distal end 24. The proximal end 22 is preferably the same diameter as the tubular body 20, and includes a plurality of proximally extending teeth 26 thereon. The teeth 26 are adapted for gripping engagement with the surface of a bone element 11 to which the bone reference assembly 10 is to be anchored. The term teeth as used herein comprises generally any substantially sharp or serrated anchoring element, adapted for piercing engagement of the bone element. These teeth preferably comprise substantially jagged projecting elements, disposed repeatedly substantially about the full circumference of the proximal end 22 of the bone reference element 12. However, they could equally comprise projecting pins or other similar extending anchoring element or elements that can be driven into the surface of the bone element and will thereby prevent rotation of the bone reference element 12 thereon. Such piecing projections can comprise as few as two or three individual elements, or can comprise a plurality of elements unevenly repeated about the proximal end of the bone reference member. Any such anchoring elements must generally be substantially sharp to enable pierce and/or gripping engagement with the bone element.

A central aperture 30 axially extends through the length of the elongated tubular body 20. The distal end 24 of the bone reference element 12 comprises a flanged end 28, to which the trackable member 16 is fastened via a fixed trackable member support rod 21. The trackable member 16 is preferably adapted to be communicable with an image guided, computer assisted surgical system capable of detecting and tracking the device in three-dimensional space within the surgical field.

The CAS bone reference assembly 10 of the present invention is preferably intended to be used in conjunction with an optical tracking CAS system which employs a network of cameras to locate the trackable member 16, or more specifically to locate identification markers 19 of a detectable element 17 thereof, so that their position and movement can be tracked during the surgery. Therefore, when the bone reference assembly 10 is fixed to the desired patient bone element 11, the anatomical position and orientation of the bone element 11 can be determined and tracked in space by the CAS system. However, a registration of the bone element must first be performed. It is to be understood that the step of performing the registration of the bone element, as used herein, comprises all means of relating the actual bone element 11 to a corresponding model or image of the same bone element. Those skilled in the art will appreciate that there are a plurality of ways of creating such a model or image of the bone element, and of relating or matching the actual bone element 11 to the model or image thereof.

Generally, a plurality of points are first acquired on the surface of the bone element 11 using a CAS system communicable probe or pointer instrument. These points can then, for example, be registered to the a corresponding virtual model of the bone element 11 generated from a computed tomography (CT) scan. Similarly, the position and orientation in 3D space of reference artifacts in anatomical images of the bone element 11 can be mathematically related to the position of the reference clamp. The principle function being to permit the bone element 11 to be matched with the corresponding anatomical image or model displayed to the surgeon on a monitor, such that the real-time position of the bone element 11, to which the present bone reference assembly 10 is fixed, can be shown graphically to the surgeon. Generally, either pre-operatively taken CT scans or intra-operative fluoroscopic images of the patient are used to create the anatomical model or image which is subsequently displayed on the monitors during the surgery to provide the surgeon with an accurate representation of the specific body parts or targeted elements of the patient.

For example, when CT-based images are being used, once the bone reference assembly 10 is securely engaged to the bone element 11, thereby fixing the bone element 11 relative to the location of the trackable member 16 of the bone reference assembly 10, the bone element 11 can then be registered to the computer model element thereof. This is preferably done by acquiring a plurality of points, either pre-determined and sequentially identified by the CAS to the surgeon or randomly selected by the surgeon, on the surface of the bone element using a well known calibrated CAS probe. The points on the physical bone element are then matched with corresponding points on the 3D model, thereby registering the CAS system bone model to the tracked position in space of the anatomical counterpart.

The anatomical models or images can also be acquired and/or generated using other methods such as magnetic resonance imaging, ultrasound and/or landmark digitization techniques. Such landmark digitization techniques permit intra-operatively acquired surface points, preferably acquired on specific predetermined landmarks of the bone element surface, to be used to create a computerized anatomical reference model of the bone element. This can eliminated the need for a CT scan, taken pre-operatively for example, to be used to generate the computer reference model of the bone element. All of the above described alternate methods of generating a computerized model or displaying image of the bone element, and of relating or matching the position and orientation of the actual bone element 11 thereto, will be understood herein to be included in the process of performing a registration of the bone element.

The trackable member 16 generally comprises the above-mentioned detectable tracker head element 17, preferably having three detectable element mounting posts 15 thereon, to which the CAS identification markers 19 are removably engageable. The detectable tracker head element 17 is engaged to the bone reference element 12 by the fixed trackable member support rod 21. To each mounting post 15 is removably fixed the identification markers 19, preferably optically detectable sphere elements. The detectable spheres 19 are preferably coated with a retro-reflective layer in order to be detected by, for example, an infrared sensor using axial illumination. Cameras of the optical CAS system can therefore detect the position of each optically detectable sphere 19 illuminated by infrared light. Each detectable marker element 19 can equally be any other type of position indicator such as a light emitting diode or detectable electromagnetic indicator, provided each can be detected by the type of sensor used by the CAS system. Although the present surgical bone reference assembly 10 is preferably adapted for use with an optically based CAS system, one skilled in the art will appreciate that in addition to the optical and electromagnetic systems mentioned above, other types of CAS systems can equivalently be used, such as, for example, those which use ultrasound or laser as a means for position identification. In such cases, it is to be understood that the detectable marker elements 19 will be such that they are able to indicate to, or be detected by, the particular CAS position identification system used.

Figure 3:
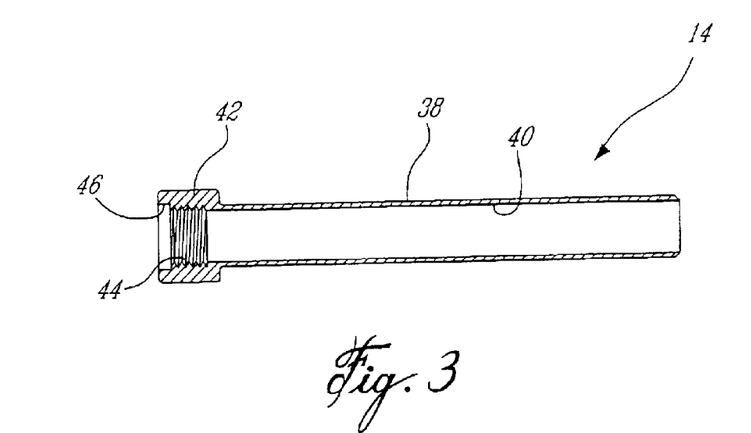
FIG. 3 is a cross-sectional longitudinal view of the protective outer sleeve of the CAS reference assembly of FIG. 1.

Referring back to FIG. 1, the bone anchoring reference element 12 is engageable within the protective outer sleeve 14. The outer sleeve 14, best seen alone in FIG. 3, comprises generally a hollow cylindrical body 38 having a central, axially extending aperture 40 throughout the length thereof. An integral distal head 42 has internal threads 44 formed therein, and also includes a larger opening 46, defined by a shoulder in the distal end of the aperture, distally of the internal threads 44. The body 38 of the sleeve 14 preferably has a length slightly shorter than the axial length of the elongated body 20 of the bone reference element 12. The central aperture 40 is diametrically sized to permit the elongated body 20 of the bone reference element 12 to be fit therein. Preferably, the clearance between the outer diameter of the elongated body 20 and the inner diameter of the sleeve body 38, is enough to permit the bone reference element to be easily slid through the sleeve 14 but not so much that there is any significant play between the two concentric parts.

The cortical or surgical screw 25 comprises bone engaging threads 27 at a proximal end thereof, machine threads 29 at a distal end thereof, and a central unthreaded portion 31. The central unthreaded portion 31 has a slightly larger diameter, and serves to help locate and guide the cortical screw 25 within the central aperture 30 of the bone reference element 12. The bone engaging threads 27 of the proximal end of the cortical screw 25 are adapted for fastening engagement with the bone element 11. The machine threads 29 at the distal end of the screw 25 correspond to those within a retention nut 33, having a radially extending proximal flange 35. The locking nut 33 is thereby engageable with the distal end of the cortical screw 25, such that the nut flange 35 can abut the annular distal surface 32 of the flanged distal end 28 of the bone reference element 12. Therefore, by tightening the retention nut 33, the bone reference element 12 is forced into contact with the bone element 11 such that the teeth 26 are pressed into the surface of the bone. The retention nut 33 and the cortical screw 25 therefore axially retain the bone reference element 12 in contact with the bone element 11. The teeth 26 are pressed into the surface of the bone and additionally prevent the bone reference element 12 from unwanted rotation relative thereto.

Figure 4:
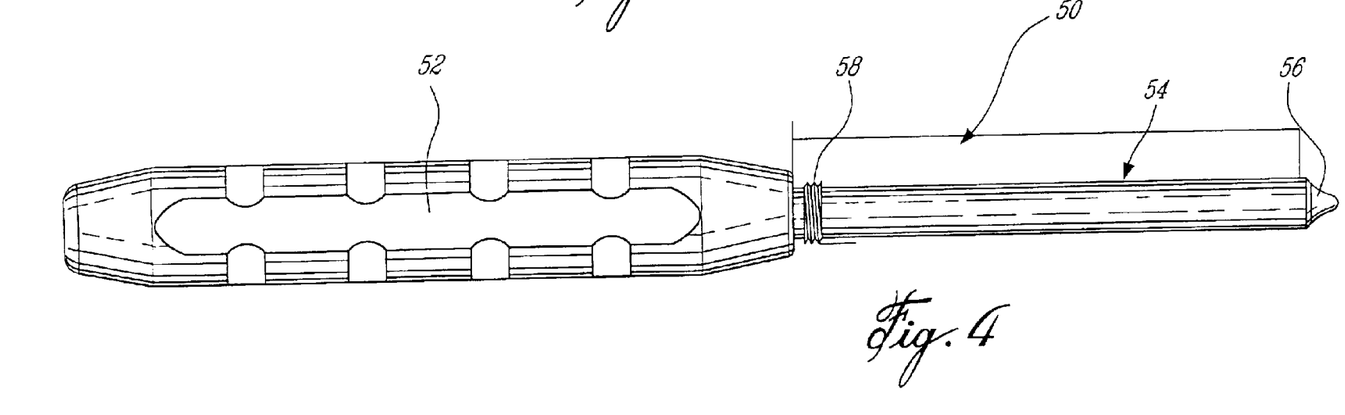
FIG. 4 is a front elevation view of a sleeve insertion probe, adapted to permit the protective outer sleeve of FIG. 3 to be removably engaged thereto.

Having generally described the elements of the present CAS bone reference assembly 10, the preferred installation method thereof will now be outlined. The protective outer sleeve 14 generally serves to act as a guide for the bone reference element 12 during insertion thereof through the soft tissue. As the teeth 26, required to securely fasten the bone reference element 12 to the bone surface, are very sharp they generally tend to cut into surrounding tissue if directly inserted through an incision in the skin. Accordingly, the present invention uses the protective sleeve 14 to guide the bone reference element 12 and enable it to be engaged with the bone surface without tearing substantially any surrounding soft tissue during the installation thereof. The protective sleeve 14 is preferable inserted first alone through a relatively small incision in the skin. Although this can be done manually, a dedicated sleeve insertion probe 50 is preferably used. As seen in FIG. 4, the sleeve insertion probe 50 comprises a handle portion 52 and a probe body 54 having a large blunt tip 56. The generally rounded blunt tip 56 enables the probe to be inserted through a surface incision and guided by the surgeon through the soft tissue without causing any significant tissue damage. Threads 58 on the distal end of the probe body 54 are adapted for engagement with the internal threads 44 within the distal head 42 of the protective sleeve 14. Accordingly, the protective sleeve 14 can be screwed onto the insertion probe 50, whose probe body 54 has a length greater than that of the sleeve 14, such that when the sleeve 14 is engaged in place on the probe 50, the rounded probe tip 56 extends beyond the end of the protective sleeve 14. While a threaded engagement is preferred, other removable fastening mechanisms can equally be used to engage the protective sleeve 14 to the probe 50 during insertion of the protective sleeve 14 through the soft tissue, providing the probe can be detached therefrom once the sleeve is in position.

As such, with the sleeve 14 in place on the insertion probe 50, the surgeon can use the probe 50 to guide the sleeve 14 through the soft tissue 13 above the bone element 11 (see FIG. 1), using the blunt probe tip 56 to palpate the bone element until a substantially central portion thereof is located. Holding the sleeve 14 in place, the probe 50 is unscrewed from the protective sleeve 14 and removed. Leaving the sleeve 14 in place, the elongated body 20 of the bone reference member 12 can then be slid down through the central aperture 40 of the sleeve 14 until the teeth 26 reach the bone surface. In this manner, the bone reference element 12 can be inserted through a relatively small skin surface incision without causing any damage, as the outer guide sleeve 14 through which it is slid prevents any contact between the sharp bone engaging teeth 26 and the surrounding soft tissue 13. The cortical screw 25 can then be inserted through the central aperture 30 of the elongated body 20 of the bone reference member 12, and screwed into engagement with the bone element 11. By adding and tightening the locking nut 33, the CAS reference assembly 10 is accordingly securely fastened to the bone element 11 without causing any significant soft tissue damage.

Figure 5A:
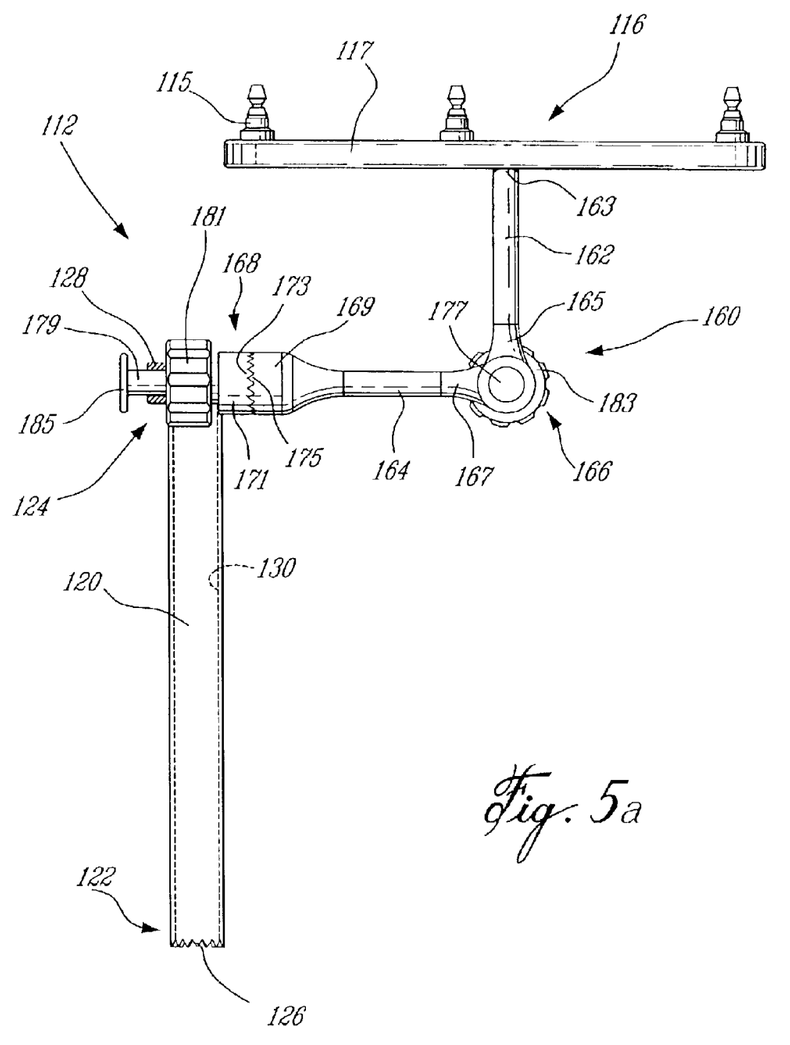
FIG. 5a is a front elevation view of an alternate embodiment of a bone reference element for the CAS reference assembly according to the present invention.
Figure 5B:
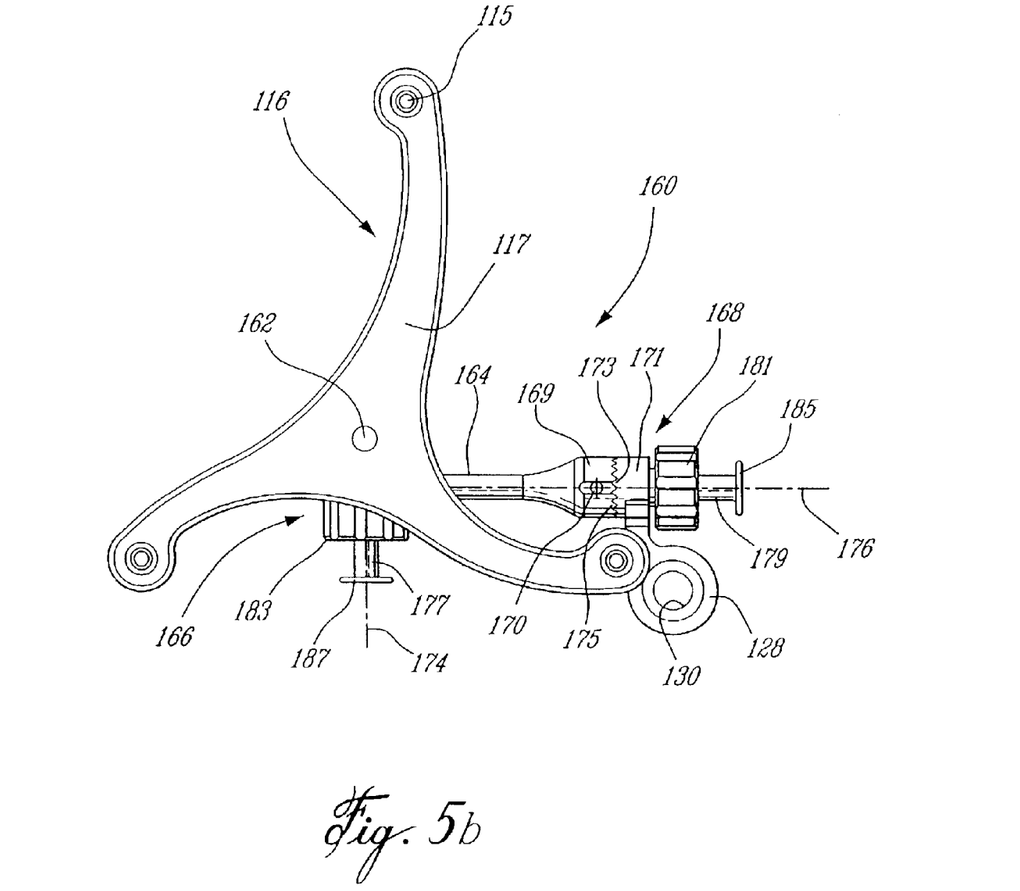
Figure 5C:
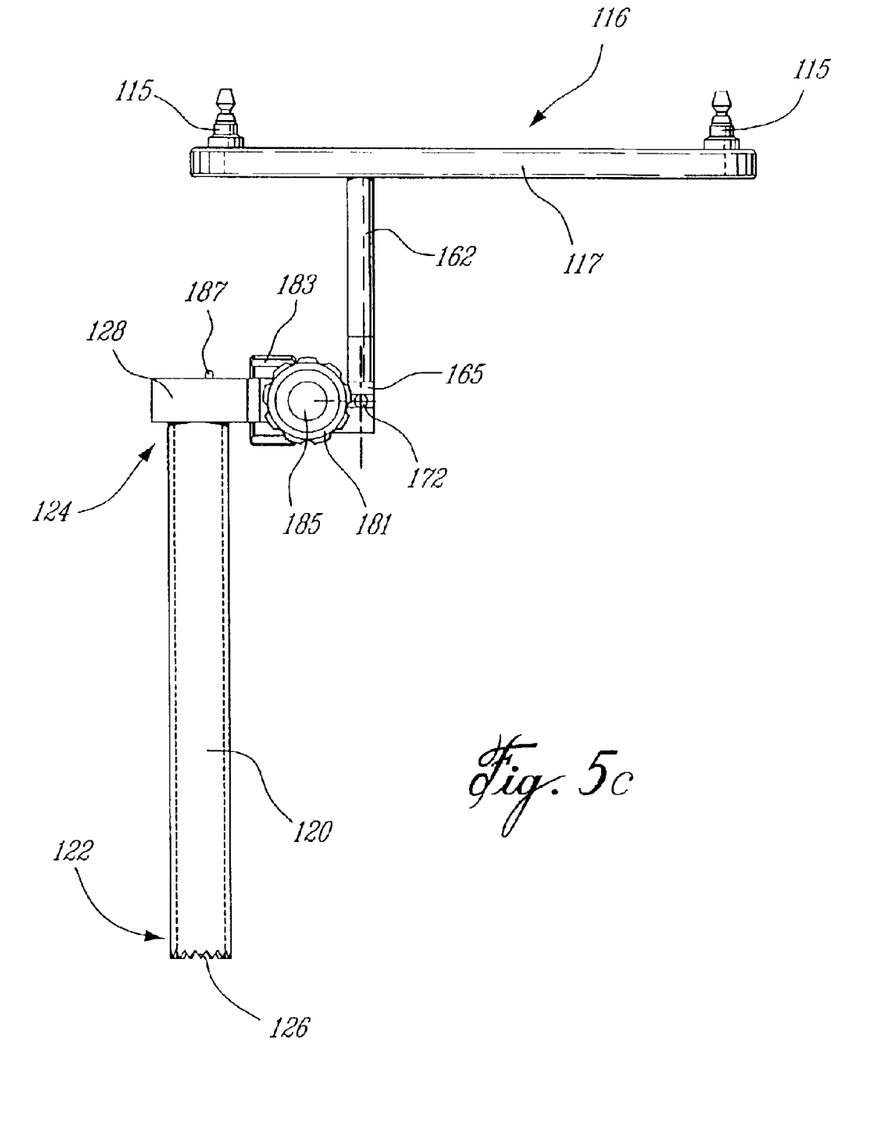

Referring now to FIGS. 5a to 5c, depicting an alternate bone reference element 112. The bone reference element 112 is similar to the bone reference element 12, generally comprising a main elongated body 120 having teeth 126 at a proximal end 122, a trackable member support mounting flange 128 at a distal end 124, and a central axially extending aperture 130 therethrough. The bone reference element 112 also similarly comprises a trackable member 116 including a tracker head element 117 having detectable element mounting posts 115 thereon. However, the bone reference element 112 further comprises an articulated trackable member support 160, in lieu of the fixed support rod 21 of the embodiment of FIG. 1. The articulated support 160 enables the location of the tracker head element 117, relative to the body of the reference element 112 fastened to the bone, to be adjusted. This can be desirable, for example, in order to ensure that the surgeon has an unobstructed access to the patient for the surgical procedure, or to ensure that the detectable elements of the trackable member 116 maintain an uninterrupted communication with the cameras or similar sensing elements of the CAS system.

The articulated support member 160 comprises a first link member 164 and a second link member 162, interconnected by a first joint 166 therebetween. The second link member 162 comprises a rigid rod element, fixed at a first end 163 to the tracker head element 117 of the trackable member 116, and having a preferably integrally formed annular second end 165 at an opposing end. The annular second end 165 includes a first joint toothed ring, disposed substantially perpendicularly to the surface of the tracker head element 117. The first joint toothed ring is preferably integrally formed with the annular second end 165 of the second link member 162. The teeth of this toothed ring inter-engage with corresponding teeth of another toothed ring, preferably integrally formed on the annular second end 167 of the first link member 164. When the two toothed rings are pressed into engagement together, the teeth interlock to prevent rotational movement relative to one another. The annular second end 165 of the second link 162 comprises a central aperture defined therethrough, about which the toothed ring is disposed. This central aperture is concentric with the first joint axis of rotation 174, substantially perpendicular to the longitudinal axes of both the first and second link members. A first joint axle pin 177 is permanently fixed at one end to the second end 165 of the second link 162, and extends through the central aperture in the annular second end 167 of the first link 164. The first joint axle pin 177 has an externally threaded central portion, not seen in the figures but disposed generally partially beneath each of the first joint locking nut 183 and the annular second end 167 of the first link 164. The central aperture has a diameter sufficiently large enough such that the axle pin 177 is free to rotate within the aperture. The axle pin 177 also comprises a disc flange 187 at the free end of the pin, opposite the end fixed to the second end 165 of the second link 162. The disc flange 187 prevents the first joint locking nut 183 from being completely separable from the first joint assembly 166. When the locking nut 183, having internal threads corresponding to those on the axle pin 177, is tightened, it forces the annular second end 167 of the first link member 164 towards the second end 165 of the second link member 162, such that the corresponding toothed rings engage one another. This thereby permits the first and second link members to be engaged in a specific angular relation to one another. The first joint assembly 166 therefore permits selective rotational adjustment of the second link member 162, to which the trackable member 116 is fastened, about the first joint axis of rotation 174.

The articulated support 160 further comprises a second joint assembly 168, providing selective rotational adjustment between the first link member 164 and the elongated body 120 of the bone reference element 112, about the second joint axis of rotation 176, collinear with the longitudinal axis of the first link member 164 and substantially perpendicular to a longitudinal axis of the elongated body 120. The second joint assembly 168 operates much as the first joint 116, permitting selective rotation of the first link member 164 relative to the main elongated body 120 of the bone reference member 112 when the second joint locking nut 181 is disengaged, and fixed engagement between the elongated body 120 and the first link member 164 when the locking nut 181 is tightened. The second joint assembly 168 includes a first end 169, disposed at an opposite end of the first link member 164 from the second end 167. The first end 169 comprises a toothed ring 175, having projecting teeth for engagement with the corresponding projecting teeth of a toothed ring 173, centrally disposed on annular support mount 171, preferably integrally formed with the distal flanged end 128 of the elongated body 120 of the bone reference member 112. Within the toothed ring 173 is the concentric aperture of the annular support mount 171, through which extends the second joint axle pin 179. A first end of the second joint axle pin 179 is permanently fastened to the first end 169 of first link member 164, in an aperture concentric with the toothed ring 175. Much as per the first joint axle pin 177, the second joint axle pin 179 has a threaded central body portion, such that the second joint locking nut 181 can be engaged thereto, thereby forcing the first link member 164 into fixed engagement with the support mount 171 of the bone anchored elongated body member 120 when the locking nut 181 is tightened. The corresponding teeth of the mating toothed rings, 175 and 173 respectively on the first end 169 of the first link member and the support mount 171 of the bone anchored elongated body member 120, are consequently engaged such that the two elements are rotationally fixed relative to one another. The second joint axle pin 179 also similarly has a radially extending flange 185 at a second end thereof, to prevent the second joint locking nut 181 from being completely removable from the second joint assembly 168, while being spaced sufficiently far on the pin 179 to permit the nut 181 to be fully unscrewed from the threads of the axle pin 179. This permits all surfaces of the joints to be completely exposable, in order to allow a thorough cleaning thereof. This also enables the locking nuts 181 and 183, although they can be fully disengaged from the threads of the joint retaining pins 179 and 177, to be permanently captive such that they can never inadvertently fall off if completely unscrewed.

Although any method can be used to permanently fasten the joint axle pin 179 within the first end 169 of the first link member 164, a small cross-pin fastener 170 is preferably used. As best seen in FIG. 5b, this small pin 170 transversely extends through the first link member first end 169 and through the second joint axle pin 179, to thereby permanently fasten them together. Similarly, a small cross-pin fastener 172 is also used to fix the first joint axle pin 177 to the second end 165 of the second link member 162, as best seen in FIG. 5c. It is to be noted that, when permanently fastening the joint axle pins 177 and 179 in both joint assemblies to their respective link member ends, the axle pins must first be threaded onto the locking nuts 183 and 181, as the free end flanges 187 and 185 of the joint axle pins 177 and 179 would prevent nuts to be installed once they are fastened in place with the cross-pin fasteners 170 and 172.

The articulated support member 160 preferably comprises at least the two above-described independently articulated joints. However, a single joint is equally foreseeable. For example, a single rotating joint can be used between the bone anchored elongated body member 120 and an angled, rigid support arm having a trackable member on the end thereof. Although providing less adjustability and range of motion, such an arrangement would be simpler and less expensive. No matter the number, each joint preferably provides an independent single degree of freedom. However, a selectively lockable ball-and-socket type joint could also be used, and would provide itself three rotational degrees of freedom. While joints providing rotational movement are preferred, other types of joints, for example those providing a translational degree of freedom, are equally possible but preferably used in combination with at least one rotational joint.

Therefore, using the articulated support 160, the location of the trackable member 116 can be selectively adjusted in order to ensure the best line-of-sight communication between the detectable marker elements on the tracker head element 117 and the cameras of the CAS system. Once the elongated body member 120 is anchored directly to the bone element as described above, and ensuring the two joint locking nuts 171 and 183 are loosened sufficiently to permit free movement of the two link members 162 and 164 of the articulated support 160, the trackable member 116 can be moved by the surgeon until it is in a desired position. This can constitute a position that best permits unobstructed access of the patient for the surgical procedure, and/or a position that best permits clear communication between the cameras or other similar position sensing elements of the CAS system and the detectable marker elements of the trackable member 116. Once the trackable member 116 is in the desired position, the joint locking nuts 181 and 183 of the articulated support assembly 160 are tightened, thereby engaging the trackable member 116 fixed relative to the bone element of the patient.

An important feature of the present bone reference assembly 10, is the ease with which all surfaces of the assembly can be cleaned. Particularly, all threaded surfaces and all joints can be sufficiently exposed such that thorough pressure cleaning is possible. The ability to pressure clean and autoclave all surfaces of surgical devices is vital to ensure that all contaminating biological matter are safely removed. Such potentially dangerous contaminating biological matter can include unwanted bacteria and prions, microscopic protein particles similar to those of a virus but lacking nucleic acid and thought to be an infectious agent responsible certain degenerative diseases of the nervous system.

The embodiments of the invention described above are intended to be exemplary only. The scope of the invention is therefore intended to be limited solely by the scope of the appended claims.

What is claimed is:

1. A method for monitoring position and movement of bone element using an image guided surgical system, comprising the steps of:
   providing a bone reference assembly comprising a toothed bone anchor member and a trackable member, the trackable member comprising a detectable element adapted to be located and tracked in three dimensional apace by the image guided surgical system, thereby defining position and movement of the trackable member;
   inserting a protective guide member through soft tissue covering the bone element using a proximal end while gradually separating the soft tissue so as not to cause significant damage thereto, until the proximal end is substantially adjacent the bone element, the protective guide member being sized to receive at least the toothed bone anchor member therein;
   using the protective guide member to guide the toothed bone anchor member into direct engagement with the bone element without damaging the soft tissue;
   engaging the toothed bone anchor member to the bone element such that the bone reference assembly is in a fixed position relative to the bone element;
   performing a registration of the bone element; and locating and tracking the bone element using the image guided surgical system.

2. The method as defined in claim 1, further comprising adjusting the trackable member, linked to the toothed bone anchor member by an adjustable articulated support, into a desired position and orientation relative to sensing elements of the image guided surgical system.

3. The method as defined in claim 2, wherein adjusting the trackable member further comprises adjusting joint of the articulated support.

4. The method as defined in claim 3, further comprising locking the joint of the articulated support such that the trackable member is fixed in the desired position relative to the bone anchor member.

5. The method as defined in claim 3, further composing adjusting at least two independent, lockable joints of the articulated support.

6. The method as defined in claim 1, further comprising inserting the toothed bone anchor member through a sleeve portion of the protective guide member.

7. The method as defined in claim 6, further comprising inserting a surgical screw through a central aperture in the to the toothed bone anchor member, a proximal end of the screw being adapted to be fastened the bone element.

8. The method as defined in claim 7, further comprising engaging a nut on a distal end of the screw and tightening the nut thereon until the nut engages the bone anchor member, the bone anchor member being thereby fixed on the surgical screw between the nut and the bone element.

9. The method as defined in claim 1, wherein inserting the protective guide member further comprises using an insertion probe having substantially blunt and conical proximal end.

10. The method as defined claim 9, further comprising engaging the protective guide member to the insertion probe prior to inserting it through the soft tissue, detaching the probe member in the protective guide member once the protective guide member is in place, and moving the probe member.

11. The method as defined in claim 1, wherein the step of performing the registration comprises acquiring a number of points on a surface of the bone element.

12. The method as defined in claim 11, wherein the step of performing the registration comprises matching the points to a corresponding surface of a computer stored representation of the bone element.

13. The method as defined in claim 12, wherein the computer stored representation is created by generating three dimensional computer model of the bone element from a computed tomograpby scan.

14. The method as defined claim 1, wherein the step of performing the registration comprises matching reference artifacts from a two-dimensional fluoroscopic image of the bone element to the location of the reference artifacts at the time the fluoroscope image was taken, position and orientation of the reference artifacts being determined by the image guided surgical system.

15. The method as defined in claim 11, wherein the points are acquired by digitizing landmarks on the surface of e bone element, and registration of the bone element farther comprises using the porn to build an anatomic reference model of the bone element.

16. A surgical bone reference assembly communicable with an image guided surgical system such that position and movement of a bone clement are monitorable, the bone reference assembly comprising:
   a bone anchor member comprising a trackable member and teeth engageable with the bone element, the trackable member comprising a detectable element adapted to be located and tracked in three dimensional space by the image guided surgical system, thereby defining position and movement of the trackable member; and
   a protective guide member for use with the bone anchor member such that the bone anchor member is in is through soft tissue covering the bone element without causing significant damage thereto;
   the bone anchor member being engageable with the bone element, such that the teeth are forced into engagement with the bone element and the bone anchor member is fastenable to the bone element in a fixed relation thereto.

17. The bone reference assembly as defined in claim 16, wherein the protective guide member comprises a sleeve member.

18. The bone reference assembly as defined in claim 17, wherein the sleeve member is cylindrical and the bone anchor member comprises a substantially tubular portion insertable within the sleeve member.

19. The bone reference assembly as defined in claim 18, wherein the substantially tubular portion comprises teeth near a proximal end thereof.

20. The bone reference assembly as defined in claim 16, wherein the sleeve member is removably engageable about a probe, adapted for inserting the sleeve member through the soft tissue without causing significant damage thereto.

21. The bone reference assembly as defined in claim 20, wherein the probe comprises a substantially blunt conical tip adapted for gradually separating the soft tissue without causing significant damage thereto.

22. The bone reference assembly as defined in claim 16, wherein the trackable member is linked to the bone anchor member by an adjustable articulated support, permitting variable positioning of the trackable member and being lockable to fix the trackable member in position relative to the bone anchor member.

23. The bone reference assembly as defined in claim 22, wherein the articulated support permits at least two degrees of freedom of the trackable member relative to the bone anchor member.

24. The bone reference assembly as defined in claim 23, wherein the articulated support comprises at least two independent joints.

25. The bone reference assembly as defined in claim 24, wherein the independent joints comprise lockable, rotational joints.

26. The bone reference assembly as defined in claim 22, wherein the articulated support permits selective positioning of the trackable member relative to the bone anchor member between predetermined fixed positions.

27. The bone reference assembly as defined in claim 17, further comprising a surgical screw for fastening the bone anchor member to the bone element, the substantially tubular portion of the bone an her member being adapted to receive the surgical screw therethrough.

28. A surgical bone reference assembly communicable with a computer assisted surgical (CAS) system such that position and movement of a bone element are monitorable, the bone reference assembly comprising:
   a bone anchor member comprising a trackable member and teeth engageable with the bone element, the trackable member comprising a detectable element adapted to be located and tracked in three dimensional space by the CAS system, thereby defining position and movement of the trackable member; and
   a protective member for use with the bone anchor member such that the teeth of the bone anchor member insertable through soft tissue covering the bone clement without causing significant damage thereto;
   the bone anchor member being engageable with the bone element such that the teeth are forced into engagement with the bone element and the bone anchor member is fastenable to the bone element in a fixed relation thereto.

29. The bone reference assembly as defined in claim 28, wherein the protective member comprises a guiding sleeve member.

30. The bone reference assembly defined in claim 29, wherein the sleeve member is cylindrical and the bone anchor member comprises a substantially tubular portion insertable within the sleeve member.

31. The bone reference assembly as defined in claim 30, wherein the substantially tubular portion comprises the teeth near a proximal end thereof.

32. The bone reference assembly defined in claim 28 further comprising a probe adapted for inserting the sleeve mom through the soft tissue without causing significant damage thereto, the sleeve m or being removably engageable about the probe.

33. The bone reference assembly defined in claim 32, wherein the probe comprises a substantially blunt conical tip adapted for gradually separating the soft tissue without causing significant damage thereto.

34. A method for monitoring position and movement of a bone element using an image guided surgical system, comprising the steps of:
   providing a bone reference assembly comprising a bone anchor member having at least three bone engaging teeth, a bone anchor screw and a trackable member, the trackable ember comprising a detectable element adapted to be located and hacked in three dimensional space by the image guided surgical system, thereby defining position and movement of the trackable member;
   inserting the bone anchor member through soft tissue covering the bone element until at least a part of the bone anchor member is in direct engagement with the bone element, while protecting the soft tissue from said teeth and gradually separating the soft tissue so as not to cause significant damage thereto;

engaging the bone element with e bone anchor screw and the teeth such that the bone reference assembly in a fixed position relative to the bone element;

performing a registration of the bone element; and locating and tracking the bone element using the image guided surgical system.

35. The method as defined in claim 34, wherein the protective member comprises a protective sleeve sized to receive the bone anchor therein, the step, of inserting the bone anchor member comprising: inserting the protective sleeve through the soft tissue such that a proximal end thereof is substantially adjacent the bone element; and subsequently inserting the bon anchor member through the protective sleeve until the bone anchor member is in direct engagement with the bone element.

36. The method as defined in claim 35, wherein the step of inserting the protective sleeve further comprises using an insertion probe having a substantially blunt and conical proximal end.

37. The method as defined in claim 36, further comprising engaging the protective sleeve to the insertion probe prior to inserting it through the soft tissue, detaching the insertion probe from the protective sleeve once in place substantially adjacent the bone element and removing the probe member leaving the protective sleeve in place.

38. The method as defined in claim 34, wherein the step of engaging the bone anchor member to the bone element includes inserting the bone anchor screw through a central aperture in the bone anchor member, and fastening the bone anchor member to the bone element using the bone anchor screw.

* * * * *